United States Patent [19]

Morris et al.

[11] 4,256,916

[45] Mar. 17, 1981

[54] OXIDATION OF POLYETHYLENE GLYCOLS TO DICARBOXYLIC ACIDS

[75] Inventors: Don L. Morris; William J. Gammans; Jerry D. Holmes, all of Longview, Tex.

[73] Assignee: Eastman Kodak Company, Rochester, N.Y.

[21] Appl. No.: 66,759

[22] Filed: Aug. 15, 1979

Related U.S. Application Data

[63] Continuation-in-part of Ser. No. 862,068, Dec. 19, 1979, abandoned.

[51] Int. Cl.³ .............................................. C07C 17/26
[52] U.S. Cl. ..................................... 562/537; 562/538
[58] Field of Search ................................ 562/537, 538

[56] References Cited

U.S. PATENT DOCUMENTS 3,929,873  12/1975  Gammans ............................ 562/537

FOREIGN PATENT DOCUMENTS 747424  11/1966  Canada ..................................... 562/538

*Primary Examiner*—Paul J. Killos
*Attorney, Agent, or Firm*—Daniel B. Reece, III; J. Frederick Thomsen

[57] ABSTRACT

Polyethylene glycols of the type

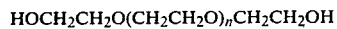

wherein n is an integer of from 0 to 5, can be converted to the corresponding dicarboxylic acids of the formula

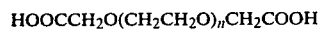

wherein n is as previously defined, by oxidation in an aqueous solution over a fixed bed catalyst consisting of platinum on a granular carbon support.

8 Claims, No Drawings

OXIDATION OF POLYETHYLENE GLYCOLS TO DICARBOXYLIC ACIDS

This is a continuation-in-part application of Ser. No. 862,068 filed Dec. 19, 1979, now abandoned.

This invention relates to an improved process for the production of dicarboxylic acids. More particularly, it relates to an improved process for the oxidation of polyethylene glycols to the corresponding dicarboxylic acids.

It is known to oxidize polyethylene glycols to the corresponding carboxylic acids with nitric acid, but this method of oxidation possesses many serious disadvantages. Thus, with the higher molecular weight glycols, hydrolysis of the ether linkages becomes appreciable. Undesirable nitrate and nitrite esters are formed which are difficult to remove, and aldehydic condensation products are also formed, which are practically impossible to remove. In addition, nitric acid must be used in excess, and the removal of the residual acid is difficult and expensive. Likewise, chromic acid has been used for similar oxidations. However, when dicarboxylic acids are produced, from about 5 to about 5.5 molecular portions of chromic acid must be used for each molecular portion of polyethylene glycol fed. Other means of attaining the desired acids are recorded, but these are of academic interest only, the processes being either too expensive or giving unsatisfactory yields. Platinum catalyzed oxidations of related alkoxyalkanols to corresponding alkoxyalkanoic acids are reported in U.S. Pat. No. 3,342,858. The inventors in that patent, however, stressed the need for carrying out the oxidation in the presence of excess caustics. More recently, in U.S. Pat. No. 3,929,873, it was disclosed that polyethylene glycols could be oxidized to their corresponding dicarboxylic acid in the presence of a catalyst selected from the group consisting of finely divided platinum, and platinum supported on carbon. The process disclosed in U.S. Pat. No. 3,929,873, while yielding excellent results when practiced in the laboratory, was not entirely suitable for commercial implementation in that it was necessary to separate the finely divided catalyst from the reaction product. This resulted in added costs for equipment necessary to physically remove the finely divided catalyst from the reaction product slurry and to recycle the catalyst to the reactor. There was also an increased loss in catalyst due to the abrasion inherent in handling a slurry of finely divided catalyst.

It is therefore an object of the present invention to improve the process disclosed in U.S. Pat. No. 3,929,873 so as to make it commercially acceptable.

A further object of the invention is to establish a process for the production of polyethylene glycols using a fixed bed catalyst.

Additional objects and advantages of this invention will be apparent from the following detailed description thereof.

The improved process described by the present invention utilizes a fixed bed catalyst consisting of platinum supported on granular carbon. The granular carbon is of a sufficient size to allow an aqueous solution of reactants to be circulated through it. Use of a fixed bed catalyst eliminates the disadvantages encountered in using a slurry catalyst, which include repeated catalyst manipulation such as filtration to remove slurried catalyst from the reaction mixture, loss of catalyst through abrasion, erosion of reactor parts, particularly pump seals, and recycle of powdered catalyst. Additionally, the method of the present invention allows the oxidaton of polyethylene glycols in higher concentrations than can be accomplished with a slurried catalyst, which higher concentrations facilitate recovery of the product dicarboxylic acids.

The oxidation of polyethylene glycol to a dicarboxylic acid over a fixed bed catalyst is found to be dependent on the rate the reactants are circulated over the catalyst surface. It is theorized that rapid circulation of the reactants over the catalyst surface is required to disrupt the stagnant liquid layer containing oxidized polyethylene glycol which accumulates at the catalyst surface. This allows fresh polyethylene glycol and oxidizing gas to reach the catalyst surface where oxidation to the dicarboxylic acid can occur.

The rate of polyethylene glycol oxidation and the selectivity for production of polyethylene glycol derived dicarboxylic acids is directly proportional to the velocity the reactants move over the catalyst surface. Use of a "trickle bed" oxidizer, which provides a minimum velocity of reactants over the catalyst surface, results in very slow oxidation of polyethylene glycol, principally to decomposition products including carbon dioxide and water. A liquid velocity of greater than 0.1 feet per second is found to be necessary for the production of polyethylene glycol derived dicarboxylic acids. The optimum velocity of reactants over the catalyst surface appears to be about 0.3 feet per second when the reaction is carried out at atmospheric pressure with oxygen as the oxidizing gas. Higher velocities may be used, but the benefits are not immediately apparent.

Other conditions employed in carrying out the oxidation using the method of the instant invention are similar to those used with the finely divided system described in U.S. Pat. No. 3,929,873, except that higher polyethylene glycol concentrations can be employed and higher temperatures can be utilized in the present invention. Polyethylene glycol concentrations in water or acetic acid of from about 5 to about 40 weight percent are found to give acceptable production rates of dicarboxylic acids. The importance of oxidation at higher concentrations of polyethylene glycol can be seen in Table 1. The amount of water that must be removed in order to recover the product is decreased dramatically when higher concentrations of polyethylene glycol are used. Increasing the polyethylene glycol concentration from 10 weight percent to 20 weight percent decreases the amount of water in the dicarboxylic acid product from 8.1 pounds per pound of product to 3.6 pounds per pound of product. The finely divided catalyst system exhibited significantly lower activity at polyethylene glycol concentrations above 15 percent. The production rate with the finely divided catalyst dropped from about 2.7 grams of diglycolic acid per gram of platinum per hour at 10 weight percent diethylene glycol feed concentration to 2.0 grams of diglycolic acid per gram of platinum per hour at 20 weight percent diethylene glycol feed concentration.

The catalyst of the instant invention is preferably from about 1 to about 10 weight percent platinum on a granular carbon support. The carbon support should have a surface area of from about 800 to about 1400 square meters per gram, and should be of a mesh size suitable for use in a fixed bed reactor, that is, the mesh should not significantly impede the flow of the aqueous solution of the reactants through the fixed bed. Catalyst mesh sizes of 4×10 and 20×30 may be employed successfully.

A reaction temperature of from about 60 to about 80° C. is preferred. Temperatures above 90° C. give low selectivity and below about 50° C. production rate drops off significantly.

The production rate of dicarboxylic acid, along with the selectivity, is also found to be related to the partial pressure of oxygen. A partial pressure of oxygen of 80 psig or greater is preferred. The use of air as a source of oxygen gives good results, although pure oxygen, because of the higher partial pressures attainable at a given total pressure, is a preferred oxidizing gas.

The reaction product can be recovered by conventional means, using distillation to remove the solvent and crystallization to further isolate the product. Yields of dicarboxylic acids product are 80 to 90 percent with quantitative conversion of polyethylene glycol routinely obtained.

The selectivity of the dicarboxylic acid formation and production rate obtained with the fixed catalyst bed are essentially the same as obtained with the finely divided catalyst.

The following examples are given to further illustrate the invention, but it is to be understood that the invention is not to be limited in any way by the details described therein.

EXAMPLE 1

This example demonstrates the oxidation of a polyethylene glycol (diethylene glycol) to form a dicarboxylic acid (diglycolic acid) using a fixed bed catalyst in a reactor employing rapid recirculation of the reaction mixture over the catalyst surface.

The reactor consists of a 1 inch by 48 inch stainless steel tube fitted to allow a gas and reaction mixture to enter at the top and exit at the base. The liquid is circulated over the catalyst using a centrifugal pump fitted to allow degassing of the reaction mixture through a condenser. The reactor can be operated at pressure of up to 150 psig.

The reactor tube contains 75 grams (0.0154 mole platinum) of 4 percent platinum on 12 by 20 mesh carbon.

The reactor is charged with 60 grams (0.566 mole) of diethylene glycol in 540 milliliters of water. Oxygen at atmospheric pressure is used as the oxidizing gas and is fed to the reactor at 200 milliliters per minute. The diethylene glycol solution is circulated over the catalyst bed at 500 milliliters per minute (approximately 0.3 feet per second velocity). The temperature is maintained at 70° C. After 8 hours the reactor is drained and the reaction mixture is concentrated to give 67 grams of a white solid which is found to contain 60.9 grams of diglycolic acid, 3.8 grams of glycolic acid and 2.2 grams of hydroxyethoxyacetic acid. The diethylene glycol is 99.8 percent converted to products. The yield of diglycolic acid is 82.8 mole percent.

EXAMPLE 2

This example demonstrates the use of air as the oxidizing gas. The conditions of Example 1 are repeated using air as the oxygen source. Air is metered to the reactor at 500 milliliters per minute. After 8 hours at 70° C. the reactor is drained. The product is a colorless oil which contains 23.4 grams of diglycolic acid, 5.4 grams of glycolic acid, and 17.1 grams of hydroxyethoxyacetic acid. The diethylene glycol is 88.6 percent converted to products. The yield of diglycolic acid is 49 percent.

EXAMPLE 3

This example shows the effect of increasing the partial pressure of oxygen by using air as the oxidizing gas at 100 psig instead of air at atmospheric pressure.

The conditions of Example 2 are repeated except the reactor is operated at 100 psig air pressure. After 8 hours at 70° C. the reactor is drained and the reaction mixture is concentrated to give 61 grams of a white solid. The solid contains 46.2 grams of diglycolic acid, 5.4 grams of glycolic acid and 8.1 grams of hydroxyethoxyacetic acid. The diethylene glycol is 99 percent converted to products. The yield of diglycolic acid is 70 mole percent.

EXAMPLE 4

This example demonstrates the effect of increasing the partial pressure of oxygen on the reaction.

The conditions of Example 1 are repeated using oxygen as the oxidizing gas at 100 psig. After 7.5 hours at 70° C. the reaction mixture is concentrated to give 70.7 grams of white solid which contains 64.8 grams of diglycolic acid, 1.9 grams glycolic acid, and 4.0 grams of hydroxyethoxyacetic acid. The diethylene glycol is 100 percent converted to products. The yield of diglycolic acid is 90.7 mole percent.

EXAMPLE 5

This example shows the effect of temperature on the oxidation of diethylene glycol. The conditions of Example 4 are repeated at 60° C., 80° C., and 90° C. The reaction time is varied to allow 99 percent conversion of diethylene glycol.

At 60° C. the yield of diglycolic acid is 89.5 percent after 7.8 hours; at 80° C. the yield is 84.0 percent after 5.5 hours; at 90° C. the yield is 71 percent after 3.0 hours.

EXAMPLE 6

This example demonstrates the effect of increasing the polyethylene glycol concentration on the rate of production of diglycolic acid from diethylene glycol in water. The example also demonstrates the dramatic decrease in the amount of water that must be removed from the product in order to recover a dry solid product.

The pressure reactor is used to oxidize 106 grams of diethylene glycol in 954 grams of water (10 weight percent), 424 grams water (20 weight percent), and 247 grams water (30 weight percent). The temperature is maintained at 80° C. and the oxygen pressure is maintained at 100 psig. The reaction is followed to determine the maximum yield of diglycolic acid at each concentration and the time required to convert all the diethylene glycol to diglycolic acid. The production rate is calculated using the formula:

$$\text{Production rate} = \frac{(\text{Percent conversion to DGA})(\text{Molecular Wt. DGA})}{(\text{Residence time})(\text{Weight of platinum})}$$

Molecular weight DGA = 134

Weight of platinum = 4.0 grams (0.02 mole)

The production rate calculated is 5.0 grams diglycolic acid per gram of platinum per hour at 10 weight percent diethylene glycol concentration, 3.6 at 20 weight percent, and 2.5 at 30 weight percent. The diglycolic acid is isolated by removing the water under the reduced pressure in a flash column for each concentration range studied. The weight of water per weight of diglycolic acid is determined and tabulated in Table 1.

TABLE 1

Effect of Diethylene Glycol Concentration on Diglycolic Acid Formation and Concentration With a Fixed Bed 4 Percent Platinum on Carbon Catalyst

| Diethylene Glycol Concentration (Weight Percent in Water) | 10% | 20% | 30% |
|---|---|---|---|
| Production rate of diglycol acid at 80° C. (grams per gram platinum per hour) | 5.0 | 3.6 | 2.5 |
| Yield of Diglycolic Acid (mole %) | 85–86% | 84–87% | 82–85% |
| Water to be vaporized in pounds for each pound of diglycolic acid recovered | 8.1 | 3.6 | 2.2 |
| U.S. Pat. No. 3,929,873 slurried catalyst production rate (grams per gram platinum per hour) | 2.7 | 2.0 | — |
| Slurried catalyst, diglycolic acid yield (mole %) | 93% | 63% | — |

Table I compares the production rate of diglycolic acid using the catalyst system of the instant invention at 80° C. and 100 psig oxygen pressure (the preferred operating conditions) with the slurried catalyst of U.S. Pat. No. 3,929,873 at 50° C. and atmospheric pressure using air (the preferred operating conditions of U.S. Pat. No. 3,929,873). Attempts to operate the slurried catalyst system at 75°–80° C. give dramatically reduced yields of diglycolic acid. Typically, the diglycolic acid yield drops to less than 70 percent. This demonstrates that the production rate of diglycolic acid, using the slurried catalyst, cannot be increased by increasing the temperature because of the severe loss in yield. The granular catalyst of the instant invention behaves differently. At 50°–60° C., the yield of diglycolic acid is 89 percent and the production rate is 1.6 grams per gram of platinum per hour. This production rate is actually lower than observed with the slurried catalyst. Increasing the temperature increases the production rate of diglycolic acid without the severe yield losses observed with the slurried catalyst system. At 80° C., the production rate is 5.0 grams per gram platinum per hour, almost twice the production rate of the slurried catalyst, and the yield is 85–86 percent. These results are shown in comparative form in Table II. The effects of temperature at higher diethylene glycol concentrations, using the slurried catalyst, were not studied in detail because of the yield losses observed at 10 percent diethylene glycol concentration.

TABLE II

Effect of Temperature on Diglycolic Acid Formation Using 10 Percent Diethylene Glycol Concentration

| Temperature, °C. | 60 | 80 |
|---|---|---|
| Production Rate of Diglcolic Acid With Catalyst of Instant Invention, grams per gram platinum per hour | 1.6 | 5.0 |
| Yield Diglycolic Acid, % | 89 | 85–86 |
| Production Rate With Slurried Catalyst of U.S. Pat. No. 3,929,873, grams per gram platinum per hour | 2.4 | 1.9 |
| Yield of Diglycolic Acid, % | 81 | 66 |

EXAMPLE 7

This example demonstrates the oxidation of triethylene glycol to ethylene bis(glycolic acid).

The pressure reactor is charged with 75 grams of triethylene glycol in 675 milliliters of water. Oxygen is used as the oxidizing gas at 100 psig.

After 8 hours at 70° C. the reaction mixture is concentrated to give 78 grams of a white solid which contained 68 grams of ethylene bis(glycolic acid), 7 grams of diglycolic acid, and 3 grams of glycolic acid. The yield of ethylene bis(glycolic acid) is 76.4 percent.

EXAMPLE 8

This example demonstrates the effect of flow rate on the oxidation of diethylene glycol.

Minimum flow conditions are studied using a 1 inch by 48 inch glass reactor containing 75 grams (0.0154 mole platinum) of a 4 percent platinum on 12 by 20 mesh carbon catalyst. This reactor is used as a trickle bed for the oxidation of a 10 weight percent diethylene glycol solution. The diethylene glycol solution, 60 grams of diethylene glycol and 540 milliliters of water, is dripped through the tube as oxygen is passed up through the base of the tube at 200 milliliters per minute. The residence time in the reactor is 8 hours. The product is concentrated to give 54 grams of a colorless liquid that contains 48 grams of diethylene glycol, 2.5 grams of diglycolic acid, and 3.5 grams of glycolic acid.

Intermediate liquid flow velocities are studied using the reactor described in Example 1.

The recirculation rate is maintained at 150 milliliters per minute (approximately 0.1 feet per second velocity) under the conditions employed in Example 1. The conversion to diglycolic acid is 48.2 percent. The recirculation rate is increased to 260 milliliters per minute (0.2 feet per second velocity). The conversion to diglycolic acid is 62.2 percent. The recirculation rate is increased to 500 milliliters per minute (0.3 feet per second velocity). The conversion to diglycolic acid increases to 80.3 percent. The recirculation rate is increased to 700 milliliters per minute (0.4 feet per second). The conversion to diglycolic acid is 79 percent.

The invention has been described in detail with particular reference to certain preferred embodiments thereof, but it will be understood that variations and modifications can be effected within the spirit and scope of the invention as described hereinabove.

I claim:

1. In a process whereby a polyethylene glycol of the formula $$HOCH_2CH_2O(CH_2CH_2O)_nCH_2CH_2OH$$

where n is an integer of from 0 to 5, is oxidized directly to a dicarboxylic acid having the formula $$HOOCCH_2O(CH_2CH_2O)_nCH_2COOH$$

wherein n is as previously defined, in the presence of a platinum catalyst selected from the group consisting of finely divided platinum and platinum supported on carbon and an oxidizing gas, the improvement resulting from passing the reactants over a fixed bed catalyst consisting of platinum deposited on granular carbon at a reactant velocity over the catalyst surface of from about 0.1 to about 0.6 feet per second and a partial pressure of oxygen of from about 30 to about 150 psig.

2. A process according to claim 1 wherein the reaction is conducted in the presence of a solvent selected from the group consisting of water and acetic acid.

3. A process according to claim 2 wherein the reactant velocity over the catalyst surface is about 0.3 feet per second and the partial pressure of oxygen is about 80 psig.

4. A process according to claim 2 wherein the temperature of reaction is from about 50° C. to about 90° C.

5. A process according to claim 1 wherein the catalyst consists of from about 1 to about 10 weight percent platinum deposited on granular carbon.

6. A process according to claim 5 wherein the granular carbon has a mesh size of from about 4×10 to about 20×30.

7. A process according to claim 2 wherein the concentration of the polyethylene glycol in the solvent is from about 5 to about 40 percent by weight.

8. A process according to claim 1 wherein the polyethylene glycol is selected from the group consisting of diethylene glycol, triethylene glycol, tetraethylene glycol, and mixtures thereof.

* * * * *